(12) United States Patent
Narasawa et al.

(10) Patent No.: US 9,875,338 B2
(45) Date of Patent: Jan. 23, 2018

(54) MEDICAL DEVICE SYSTEM AND METHOD FOR SHARING MEMORY IN MEDICAL DEVICE SYSTEM

(71) Applicant: OLYMPUS CORPORATION, Hachioji-shi, Tokyo (JP)

(72) Inventors: Takahiro Narasawa, Tokyo (JP); Akihiro Ukai, Tokyo (JP); Yasuhisa Seki, Tokyo (JP); Masanao Hara, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/467,375

(22) Filed: Mar. 23, 2017

(65) Prior Publication Data

US 2017/0193166 A1  Jul. 6, 2017

Related U.S. Application Data

(63) Continuation of application No. PCT/JP2016/067264, filed on Jun. 9, 2016.

(30) Foreign Application Priority Data

Jun. 16, 2015  (JP) ................................ 2015-121486

(51) Int. Cl.
*G06F 13/10* (2006.01)
*G06F 19/00* (2011.01)
(Continued)

(52) U.S. Cl.
CPC .......... *G06F 19/322* (2013.01); *A61B 1/0002* (2013.01); *G06F 12/023* (2013.01); *G06F 2212/254* (2013.01)

(58) Field of Classification Search
CPC .......................... G06F 19/322; A61B 1/0002
(Continued)

(56) References Cited

U.S. PATENT DOCUMENTS

2003/0191916 A1\* 10/2003 McBrearty .......... G06F 11/1464
711/162
2008/0091065 A1  4/2008 Oshima et al.
2009/0083393 A1  3/2009 Mizukami

FOREIGN PATENT DOCUMENTS

JP  2002-373084 A  12/2002
JP  2008-086666 A  4/2008
(Continued)

OTHER PUBLICATIONS

Aug. 30, 2016 International Search Report issued in Patent Application No. PCT/JP2016/067264.
(Continued)

*Primary Examiner* — Jae Yu
(74) *Attorney, Agent, or Firm* — Oliff PLC (57) ABSTRACT

A medical device system includes a first medical device, a first memory corresponding to the first medical device, a second medical device, and a second memory corresponding to the second medical device, wherein the first medical device includes a first writing unit that dynamically writes, into an area included in the first memory, definition data that defines a method for using the area and data corresponding to the definition data, and the second medical device includes a second writing unit that dynamically writes, into an area included in the second memory, definition data that defines a method for using the area and data corresponding to the definition data.

13 Claims, 6 Drawing Sheets

(51) Int. Cl.
*A61B 1/00* (2006.01)
*G06F 12/02* (2006.01)

(58) Field of Classification Search
USPC .......................................................... 711/148
See application file for complete search history.

(56) References Cited

FOREIGN PATENT DOCUMENTS

| | | |
|---|---|---|
| JP | 2008-086667 A | 4/2008 |
| JP | 2009-080569 A | 4/2009 |
| JP | 2012-221282 A | 11/2012 |

OTHER PUBLICATIONS

Aug. 30, 2016 Written Opinion issued in Patent Application No. PCT/JP2016/067264.
Dec. 6, 2016 Office Action issued in Japanese Patent Application No. 2016-559659.

* cited by examiner

MEDICAL DEVICE SYSTEM AND METHOD FOR SHARING MEMORY IN MEDICAL DEVICE SYSTEM

CROSS-REFERENCE TO RELATED APPLICATIONS

This application is based upon and claims the benefit of priority of the prior Japanese Patent Application No. 2015-121486, filed Jun. 16, 2015, the entire contents of which are incorporated herein by reference.

This is a Continuation Application of PCT Application No. PCT/JP2016/067264, filed Jun. 9, 2016, which was not published under PCT Article 21(2) in English.

FIELD

The present invention relates to a medical device system that includes a plurality of medical devices and a plurality of memories provided corresponding to the plurality of medical devices, and to a method for sharing a memory in the medical device system.

BACKGROUND

As an example of a medical device system that includes a plurality of medical devices, there has been a conventional medical device system in which a medical device that has detected an anomaly in an apparatus reports the anomaly to the other medical devices at the same time. However, reporting an anomaly to the other medical devices at the same time in this medical device system actually means that the anomaly is reported sequentially from one medical device to another. Thus, if an untransmitted piece of data destined for another medical device is still left when an anomaly in the apparatus has been detected, a delay in reporting the anomaly will occur due to the untransmitted piece of data.

Further, as another example of a medical device system that includes a plurality of medical devices, there has also been a medical device system (hereinafter referred to as a "memory-sharing-type medical device system") in which a shared memory area is provided in a memory included in each of the medical devices and latest pieces of device state data of the plurality of medical devices are recorded in the shared memory area. According to the memory-sharing-type medical device system, each of the medical devices can check states of the other medical devices by periodically monitoring the shared memory area of the memory provided therein, which results in, for example, performing the above-described reporting of an anomaly promptly without any delay.

With respect to the memory-sharing-type medical device system, the following system is known. For example, an endoscopic system in which a shared area is provided in a memory included in each of a plurality of peripheral devices and pieces of data of setting information or the like of the plurality of peripheral devices are recorded in the shared areas (see, for example, Japanese Laid-open Patent Publication No. 2008-86666).

In the conventional memory-sharing-type medical device system, it is possible to share fixed data between a plurality of medical devices using a memory included in each of the plurality of medical devices.

SUMMARY

An aspect of the present invention provides a medical device system including: a first medical device; a first memory provided corresponding to the first medical device; a second medical device; and a second memory provided corresponding to the second medical device, wherein the first memory includes a first shared memory area provided corresponding to the first medical device and a second shared memory area provided corresponding to the second medical device; the second memory includes a third shared memory area provided corresponding to the first medical device and a fourth shared memory area provided corresponding to the second medical device; the first medical device includes a first writing unit that dynamically writes, into a certain memory area included in the first shared memory area, definition data that defines a method for using the certain memory area and data corresponding to the definition data; and the second medical device includes a second writing unit that dynamically writes, into a certain memory area included in the fourth shared memory area, definition data that defines a method for using the certain memory area and data corresponding to the definition data.

Another aspect of the present invention provides a method for sharing a memory in a medical device system that includes a first medical device, a first memory provided corresponding to the first medical device, a second medical device, and a second memory provided corresponding to the second medical device, wherein the first memory includes a first shared memory area provided corresponding to the first medical device and a second shared memory area provided corresponding to the second medical device, and the second memory includes a third shared memory area provided corresponding to the first medical device and a fourth shared memory area provided corresponding to the second medical device, the method comprising: dynamically writing, by the first medical device and into a certain memory area included in the first shared memory area, definition data that defines a method for using the certain memory area and data corresponding to the definition data; dynamically writing, by the second medical device and into a certain memory area included in the fourth shared memory area, definition data that defines a method for using the certain memory area and data corresponding to the definition data; periodically reading, by the first medical device, data written into the fourth shared memory area and writing, by the first medical device, the read data into the second shared memory data, such that data written into the second shared memory area is identical to the data written into the fourth shared memory area; periodically reading, by the second medical device, data written into the first shared memory area and writing, by the second medical device, the read data into the third shared memory data, such that data written into the third shared memory area is identical to the data written into the first shared memory area; reading, by the first medical device, the data written into the second shared memory area; and reading, by the second medical device, the data written into the third shared memory area.

DESCRIPTION OF EMBODIMENTS

Embodiments of the present invention will now be described with reference to the drawings.

Figure 1:
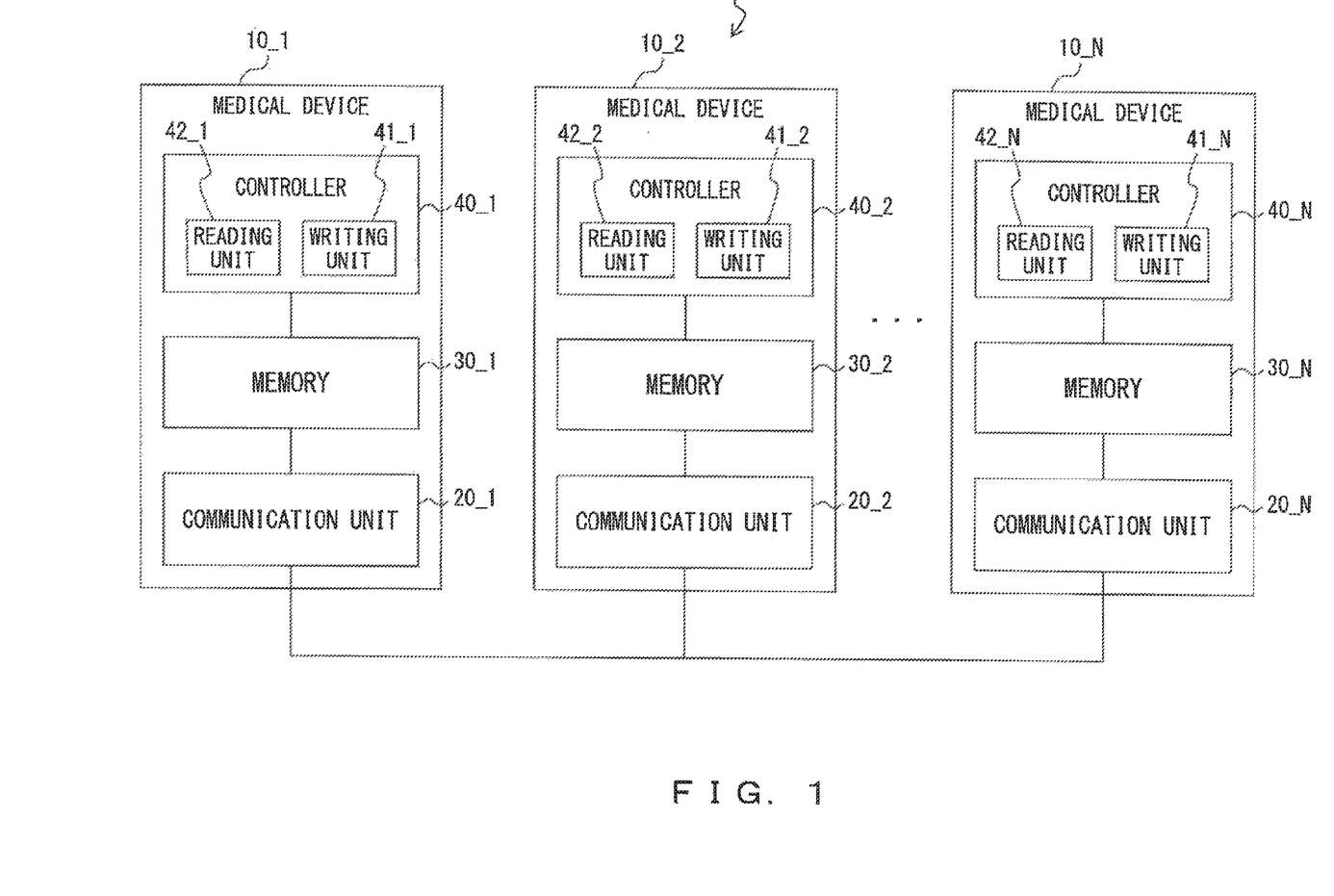
FIG. 1 illustrates an example of a configuration of a medical device system according to an embodiment.
Figure 2:
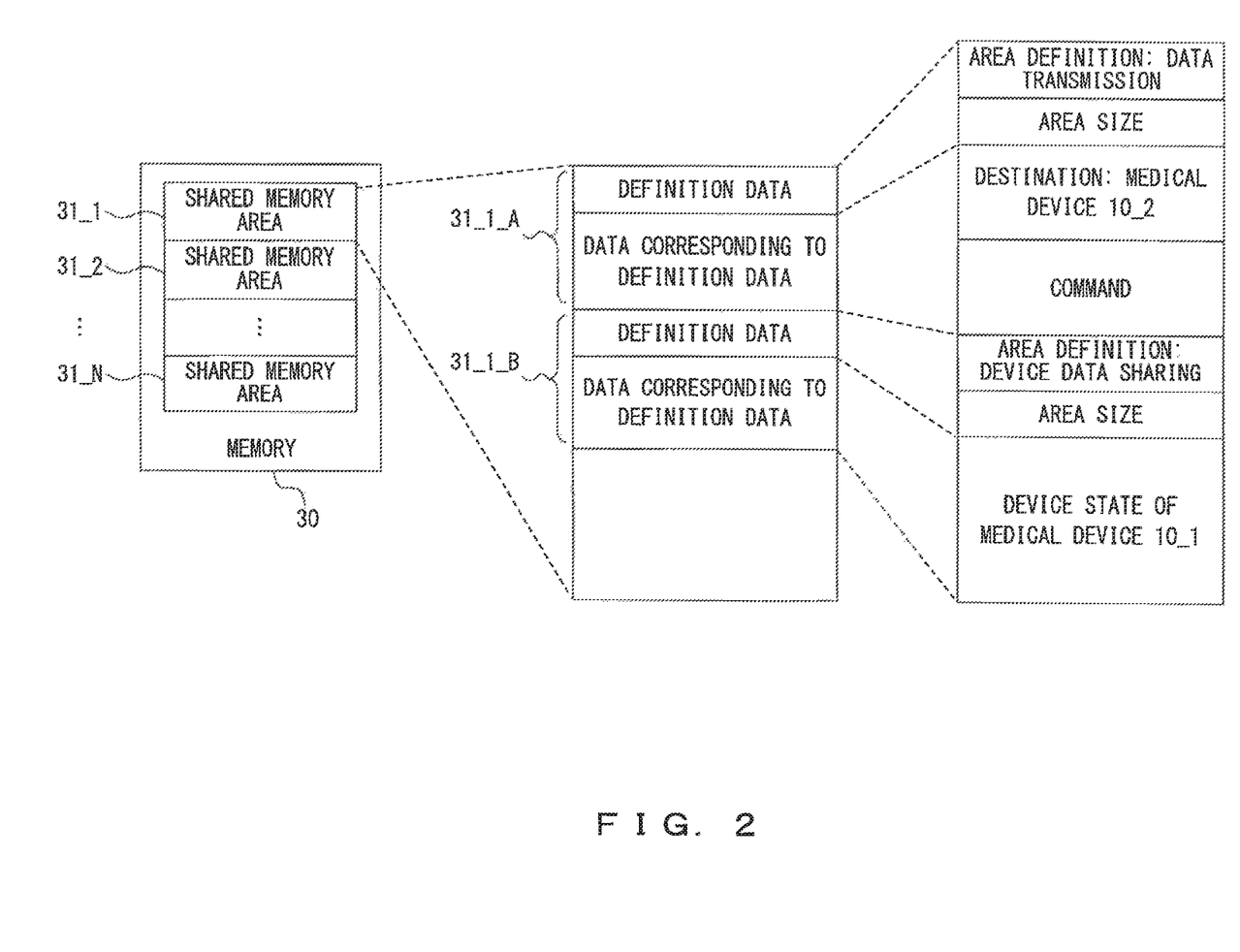
FIG. 2 illustrates an example of a data configuration of a memory included in each of a plurality of medical devices that are included in the medical device system according to the embodiment.

FIG. 1 illustrates an example of a configuration of a medical device system according to an embodiment of the present invention. FIG. 2 illustrates an example of a data configuration of a memory included in each of a plurality of medical devices that are included in the medical device system according to the present embodiment.

As illustrated in FIG. 1, a medical device system 1 according to the present embodiment includes a plurality of medical devices 10 (10_1, 10_2, . . . , and 10_N) (N medical devices). Further, the plurality of medical devices 10 are connected to one another over a wire such as through a cable, so that each medical device 10 is able to transmit/receive data to/from another medical device 10.

The medical device system 1 according to the present embodiment is, for example, an endoscopic system used for an endoscopic examination or the like, and a peripheral device for endoscope, a PC (personal computer), and a printer are examples of the plurality of medical devices 10.

Each of the medical devices 10 includes a communication unit 20, a memory 30, and a controller 40. Specifically, the medical device 10_1 includes a communication unit 20_1, a memory 30_1, and a controller 40_1, the medical device 10_2 includes a communication unit 20_2, a memory 30_2, and a controller 40_2, . . . , and the medical device 10_N includes a communication unit 20N, a memory 30_N, and a controller 40_N.

In each of the medical devices 10 in the medical device system 1 according to the present embodiment, the memory 30 is provided inside the medical device 10, but it may be provided outside the medical device 10.

As illustrated in FIG. 2, the memory 30 of each of the medical devices 10 includes a plurality of shared memory areas 31 (31_1, 31_2, . . . , and 31_N) (N shared memory areas) that are provided corresponding to the plurality of medical devices 10 (N medical devices). Specifically, the memory 30 of each of the medical devices 10 includes the shared memory area 31_1 that is provided corresponding to the medical device 10_1, the shared memory area 31_2 that is provided corresponding to the medical device 10_2, . . . , and the shared memory area 31_N that is provided corresponding to the medical device 10_N.

The communication unit 20 of each of the medical devices 10 accesses the memory 30 of each of the other medical devices 10 periodically and performs the following operation every time an access is performed: a communication unit 20 which has performed such an access reads data written into a shared memory area 31 that is included in an accessed memory 30 and that corresponds to a medical device 10 including the accessed memory 30. Then, the communication unit 20 writes the read data into a corresponding shared memory area 31 of a memory 30 that is included in a medical device 10 including the communication unit 20 which has performed an access, and performs synchronization of data between the corresponding shared memory areas 31. This permits the pieces of data written into the plurality of shared memory areas 31 (N shared memory areas) to be identical data in the memory 30 of each of the medical devices 10.

For example, when the communication unit 20_1 of the medical device 10_1 accesses the memory 30_2 of the medical device 10_2, the communication unit 20_1 reads data written into the shared memory area 31_2 of the memory 30_2. Then, the communication unit 20_1 writes the read data into the shared memory area 31_2 of the memory 30_1, and performs synchronization of data between the corresponding shared memory areas 31_2. Further, for example, when the communication unit 20_2 of the medical device 10_2 accesses the memory 30_1 of the medical device 101, the communication unit 20_2 reads data written into the shared memory area 31_1 of the memory 30_1. Then, the communication unit 20_2 writes the read data into the shared memory area 31_1 of the memory 30_2, and performs synchronization of data between the corresponding shared memory areas 31_1.

The controller 40 of each of the medical devices 10 controls the overall operation of the medical device 10 and includes a writing unit 41 and a reading unit 42. Specifically, a controller 40_1 of the medical device 10_1 controls the overall operation of the medical device 10_1 and includes a writing unit 41_1 and a reading unit 42_1, a controller 40_2 of the medical device 10_2 controls the overall operation of the medical device 10_2 and includes a writing unit 41_2 and a reading unit 42_2, . . . , and a controller 40_N of the medical device 10_N controls the overall operation of the medical device 10N and includes a writing unit 41_N and a reading unit 42_N.

The writing unit 41 of each of the medical devices 10 dynamically writes, into a certain memory area included in the shared memory area 31 of the memory 30 included in the medical device 10 including the writing unit 41, definition data that defines a method for using the certain memory area and data corresponding to the definition data, wherein the shared memory area 31 corresponds to the medical device 10 including the writing unit 41, and the definition data includes data of an area size of the certain memory area (which is also data specifying a range of the certain memory area).

For example, the writing unit 41_1 of the medical device 10_1 dynamically writes, into a certain memory area included in the shared memory area 31_1 of the memory 30_1, definition data that defines a method for using the certain memory area and data corresponding to the definition data. Further, for example, the writing unit 41_2 of the medical device 10_2 dynamically writes, into a certain memory area included in the shared memory area 31_2 of the memory 302, definition data that defines a method for using the certain memory area and data corresponding to the definition data. Furthermore, for example, the writing unit 41_N of the medical device 10_N dynamically writes, into a certain memory area included in the shared memory area 31_N of the memory 30_N, definition data that defines a method for using the certain memory area and data corresponding to the definition data.

Here, when the writing unit 41_1 of the medical device 10_1 dynamically writes the definition data and the data corresponding to the definition data into the certain memory area included in the shared memory area 31_1 of the memory 30_1, the writing unit 41_1 writes, for example, data illustrated in FIG. 2. Specifically, for example as illustrated in FIG. 2, the writing unit 41_1 writes, into a memory area 31_1_A included in the shared memory area 31_1 of the memory 30_1 and as definition data that defines a method for using the memory area 31_1_A, data that defines the memory area 31_1_A being used for data transmission ("area definition: data transmission") and data of an area size of the memory area 31_1_A ("area size"). The writing unit 41_1 also writes, as data corresponding to the definition data described above, command data ("command") and destination data ("destination: medical device 10_2") indicating that the command data is to be destined for the medical device 10_2. Further, for example as illustrated in FIG. 2, the writing unit 41_1 writes, into a memory area 31_1_B included in the shared memory area 31_1 of the memory 30_1 and as definition data that defines a method for using the memory area 31_1_B, data that defines the memory area 31_1_B being used for sharing device state data of the medical device 10_1 ("area definition: device data sharing") and data of an area size of the memory area 31_1_B ("area size"). The writing unit 41_1 also writes the device state data of the medical device 10_1 ("device state of medical device 10_1") as data corresponding to the definition data described above. The shared memory area 31_1 of the memory 30_1 is dynamically divided into areas by the writing unit 41_1 writing data dynamically into the shared memory area 31_1 of the memory 30_1.

The reading unit 42 of each of the medical devices 10 reads data written into the shared memory area 31 of the memory 30 included in the medical device 10 including the reading unit 42.

For example, the reading unit 42_1 of the medical device 10_1 reads data written into the shared memory area 31 of the memory 30_1. Further, for example, the reading unit 42_2 of the medical device 10_2 reads data written into the shared memory area 31 of the memory 30_2. Furthermore, for example, the reading unit 42_N of the medical device 10_N reads data written into the shared memory area 31 of the memory 30_N.

However, the reading unit 42 of each of the medical devices 10 does not read data destined for any of the medical devices 10 other than the medical device 10 including the reading unit 42. Thus, for example, the reading unit 42_1 of the medical device 10_1 does not read data destined for the medical device 10_2 or the medical device 10_N. Further, the reading unit 42 of each of the medical devices 10 also does not read data written into the shared memory area 31 which corresponds to the medical device 10 including the reading unit 42 (which is also data written by the writing unit 41 included in the medical device 10 including the reading unit 42). Thus, for example, the reading unit 42_1 of the medical device 10_1 also does not read data written into the shared memory area 31_1 corresponding to the medical device 10_1 (which is also data written by the writing unit 41_1).

In the medical device system 1 having the configuration described above, the controller 40 of each of the medical devices 10 is configured to include, for example, a processor such as a CPU and a memory such as a RAM or a ROM, and the overall operation of the medical device 10 including the controller 40 is controlled by the processor executing a program stored in the memory, which results in realizing the writing unit 41 and the reading unit 42 of the controller 40. The communication unit 20 of each of the medical devices 10 is configured by, for example, a communication interface device that permits its medical device 10 to be communicatively connected to the other medical devices 10.

Further, in the medical device system 1 having the configuration described above, the medical device 10_1 is an example of a first medical device, and the medical device 10_2 is an example of a second medical device. The memory 30_1 is an example of a first memory provided corresponding to the first medical device, and the memory 30_2 is an example of a second memory provided corresponding to the second medical device. In the memory 30_1, the shared memory area 31_1 is an example of a first shared memory area provided corresponding to the first medical device, and the shared memory area 31_2 is an example of a second shared memory area provided corresponding to the second medical device. In the memory 30_2, the shared memory area 31_1 is an example of a third shared memory area provided corresponding to the first medical device, and the shared memory area 31_2 is an example of a fourth shared memory area provided corresponding to the second medical device. The writing unit 41_1 is an example of a first writing unit that dynamically writes, into a certain memory area included in the first shared memory area, definition data that defines a method for using the certain memory area and data corresponding to the definition data. The writing unit 41_2 is an example of a second writing unit that dynamically writes, into a certain memory area included in the fourth shared memory area, definition data that defines a method for using the certain memory area and data corresponding to the definition data. The communication unit 20_1 is an example of a first synchronization unit that periodically reads data written into the fourth shared memory area and writes the read data into the second shared memory area, such that data written into the second shared memory area is identical to the data written into the fourth shared memory area. The communication unit 20_2 is an example of a second synchronization unit that periodically reads data written into the first shared memory area and writes the read data into the third shared memory area, such that data written into the third shared memory area is identical to the data written into the first shared memory area. The reading unit 42_1 is an example of a first reading unit that reads the data written in the second shared memory area. The reading unit 42_2 is an example of a second reading unit that reads the data written in the third shared memory area.

Next, an operation of data transmission/reception performed between the plurality of medical devices 10 is described as an operation of the medical device system 1 according to the present embodiment. Here, as an example of the operation, an operation of data transmission/reception performed between the medical device 10_1 and the medical device 10_2 is described using FIGS. 3A, 3B, 4A, and 4B.

Figure 3A:
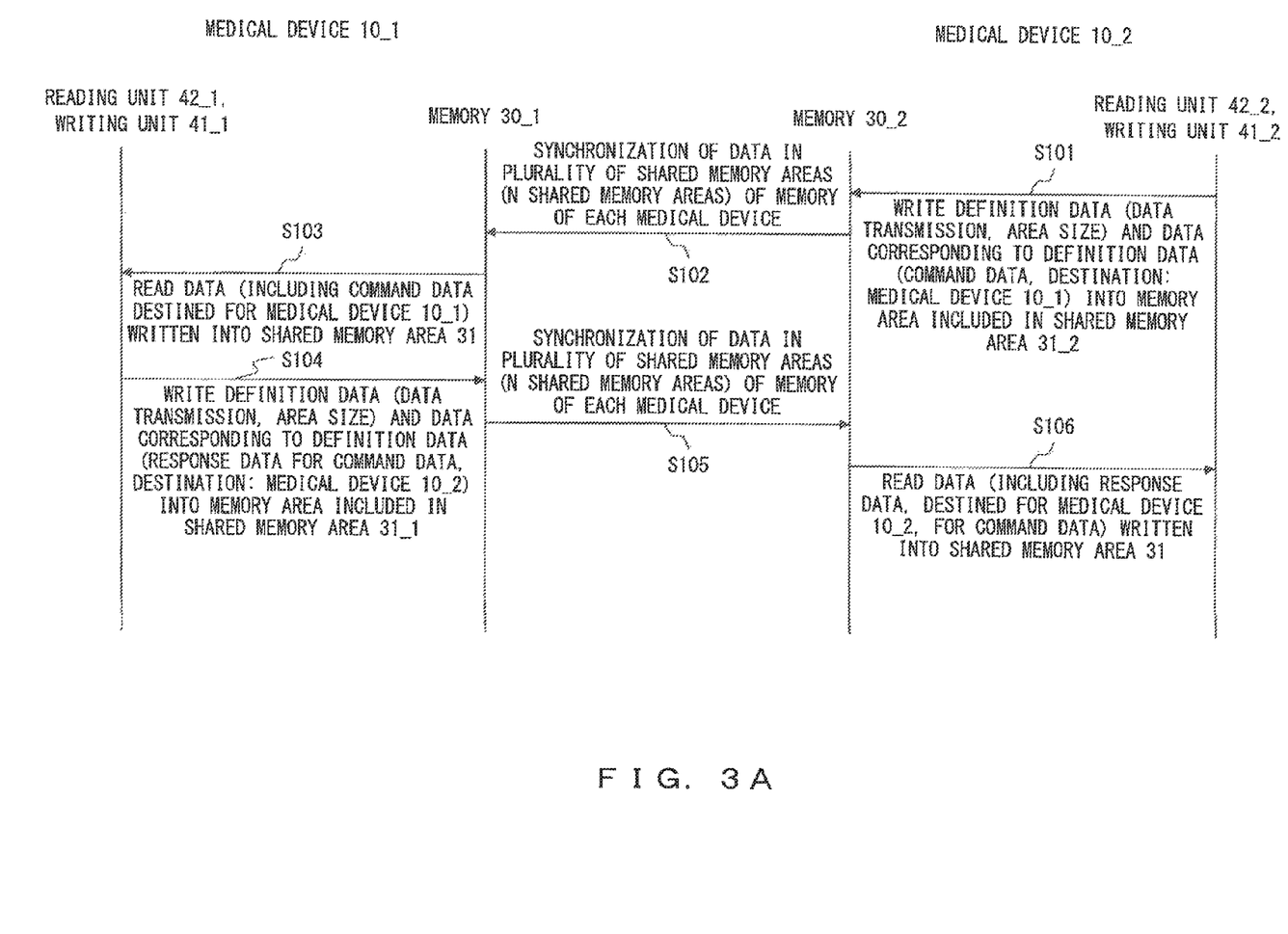
FIG. 3A is a sequence diagram (part 1) that illustrates an example of an operation performed when transmissions of command data and response data for the command data are performed between two medical devices.
Figure 3B:
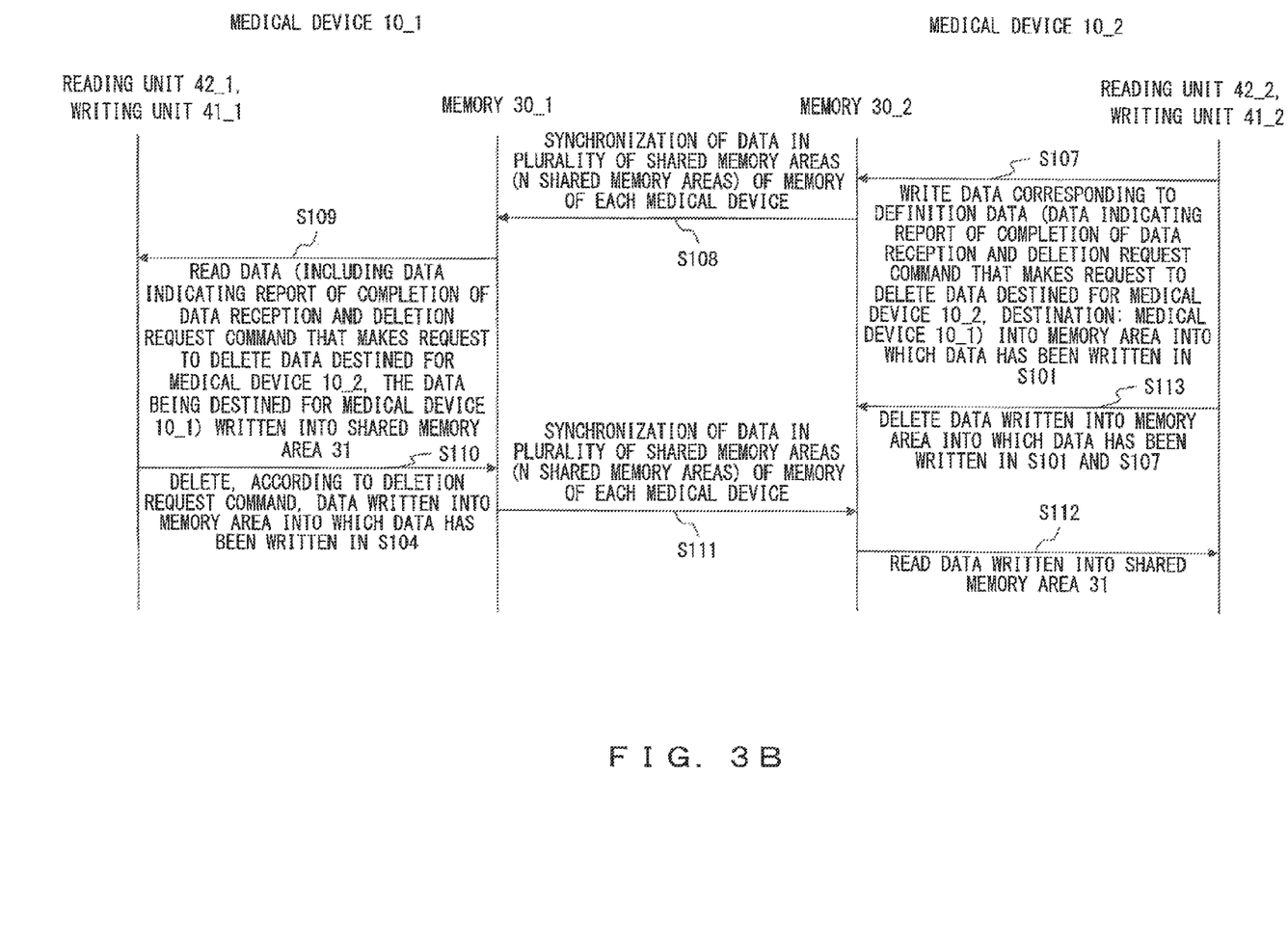
FIG. 3B is the sequence diagram (part 2) that illustrates an example of an operation performed when transmissions of command data and response data for the command data are performed between two medical devices.

FIGS. 3A and 3B are a sequence diagram that illustrates an example of an operation performed when command data is transmitted from the medical device 10_2 to the medical device 10_1 and response data for the command data is transmitted from the medical device 10_1 to the medical device 10_2.

As illustrated in FIGS. 3A and 3B, in this operation, first, the writing unit 41_2 of the medical device 10_2 writes, into a certain memory area included in the shared memory area 31_2 of the memory 30_2 and as definition data that defines a method for using the certain memory area, data that defines the certain memory area being used for data transmission and data of an area size of the certain memory area, and writes, into the certain memory area and as data corresponding to the definition data, command data and destination data indicating that the command data is to be destined for the medical device 10_1 (S101).

After that, synchronization of data is performed in the plurality of shared memory areas 31 (N shared memory areas) of the memory 30 of each of the medical devices 10 (S102). In S102, for example, the communication unit 20_1 of the medical device 10_1 reads data written into the shared memory area 31_2 of the memory 30_2 of the medical device 10_2 and writes the data into the shared memory area 31_2 of the memory 30_1.

Next, the reading unit 42_1 of the medical device 10_1 reads data written into the shared memory area 31 of the memory 30_1 (S103). In S103, for example, the reading unit 42_1 reads the command data destined for the medical device 10_1 from the shared memory area 31_2 of the memory 30_1.

Next, the writing unit 41_1 of the medical device 10_1 writes, into a certain memory area included in the shared memory area 31_1 of the memory 30_1 and as definition data that defines a method for using the certain memory area, data that defines the certain memory area being used for data transmission and data of an area size of the certain memory area, and writes, into the certain memory area and as data corresponding to the definition data, response data for the command data read in S103 and destination data indicating that the response data is to be destined for the medical device 10_2 (S104).

After that, synchronization of data is performed in the plurality of shared memory areas 31 (N shared memory areas) of the memory 30 of each of the medical devices 10 (S105). In S105, for example, the communication unit 20_2 of the medical device 10_2 reads data written into the shared memory area 31_1 of the memory 30_1 of the medical device 10_1 and writes the data into the shared memory area 31_1 of the memory 30_2.

Next, the reading unit 42_2 of the medical device 10_2 reads data written into the shared memory area 31 of the memory 30_2 (S106). In S106, for example, the reading unit 42_2 reads, from the shared memory area 31_1 of the memory 30_2, the response data, destined for the medical device 10_2, for the command data.

Next, as data corresponding to the definition data, the writing unit 41_2 of the medical device 10_2 writes, into the certain memory area which is included in the shared memory area 31_2 of the memory 30_2 and into which data has been written in S101, data indicating a report of a completion of data reception and a deletion request command that makes a request to delete data destined for the medical device 10_2, and destination data indicating that the data indicating the report and the deletion request command is to be destined for the medical device 10_1 (S107).

After that, synchronization of data is performed in the plurality of shared memory areas 31 (N shared memory areas) of the memory 30 of each of the medical devices 10 (S108). In S108, for example, the communication unit 20_1 of the medical device 10_1 reads data written into the shared memory area 31_2 of the memory 30_2 of the medical device 10_2 and writes the data into the shared memory area 31_2 of the memory 30_1, as in the case of S102.

Next, the reading unit 42_1 of the medical device 10_1 reads data written into the shared memory area 31 of the memory 30_1 (S109). In S109, for example, the reading unit 42_1 reads, from the shared memory area 31_2 of the memory 30_1, the data destined for the medical device 10_1 which indicates a report of a completion of data reception and a deletion request command that makes a request to delete data destined for the medical device 10_2.

Next, according to the deletion request command, the writing unit 41_1 of the medical device 10_1 deletes data written into the certain memory area which is included in the shared memory area 31_1 of the memory 30_1 and into which data has been written in S104 (S110).

After that, synchronization of data is performed in the plurality of shared memory areas 31 (N shared memory areas) of the memory 30 of each of the medical devices 10 (S111). In S111, for example, the communication unit 20_2 of the medical device 10_2 reads data written into the shared memory area 31_1 of the memory 30_1 of the medical device 10_1 and writes the data into the shared memory area 31_1 of the memory 30_2, as in the case of S105. Accordingly, data written into a certain memory area that is included in the shared memory area 31_1 of the memory 30_2 and that corresponds to the certain memory area from which data has been deleted in S110 is also deleted.

Next, the reading unit 42_2 of the medical device 10_2 reads data written into the shared memory area 31 of the memory 30_2 (S112).

During a period of time from the point at which the process of S108 is terminated to the point just before the process of S111 is started, in the medical device 10_2, the writing unit 41_2 deletes data written into the certain memory area which is included in the shared memory area 31_2 of the memory 30_2 and into which data has been written in S101 and S107 (S113). Accordingly, in S111 described above, the communication unit 20_1 of the medical device 10_1 reads data written into the shared memory area 31_2 of the memory 30_2 of the medical device 10_2 and writes the data into the shared memory area 31_2 of the memory 30_1, which results in also deleting data written into a certain memory area that is included in the shared memory area 31_2 of the memory 30_1 and that corresponds to the certain memory area from which data has been deleted in S113.

The operation illustrated in FIGS. 3A and 3B permits, for example, transmission of command data from the medical device 10_2 to the medical device 10_1, and transmission of response data for the command data from the medical device 10_1 to the medical device 10_2.

Figure 4A:
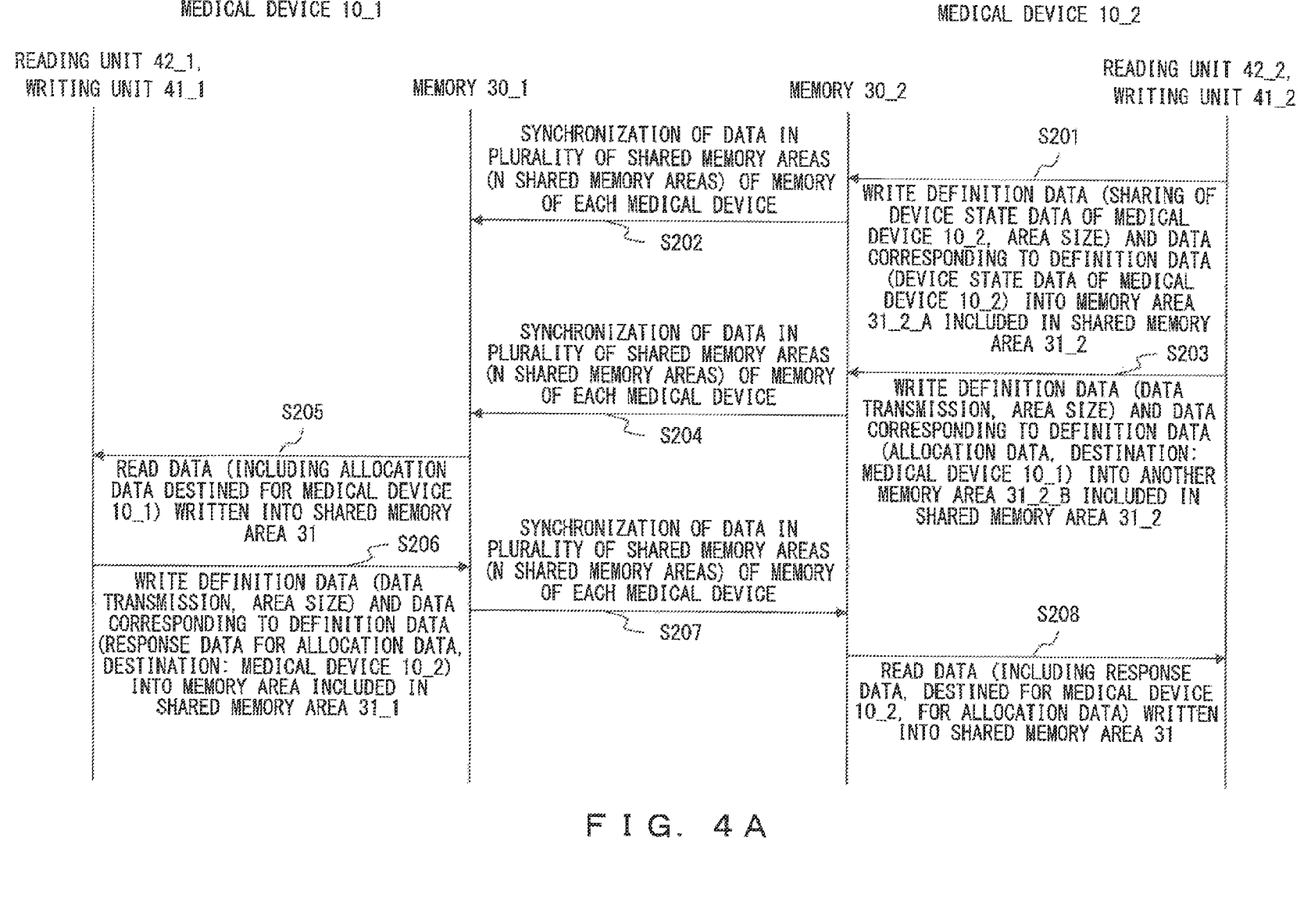
FIG. 4A is a sequence diagram (part 1) that illustrates an example of an operation performed when necessary device state data of a certain medical device is read by another medical device.
Figure 4B:
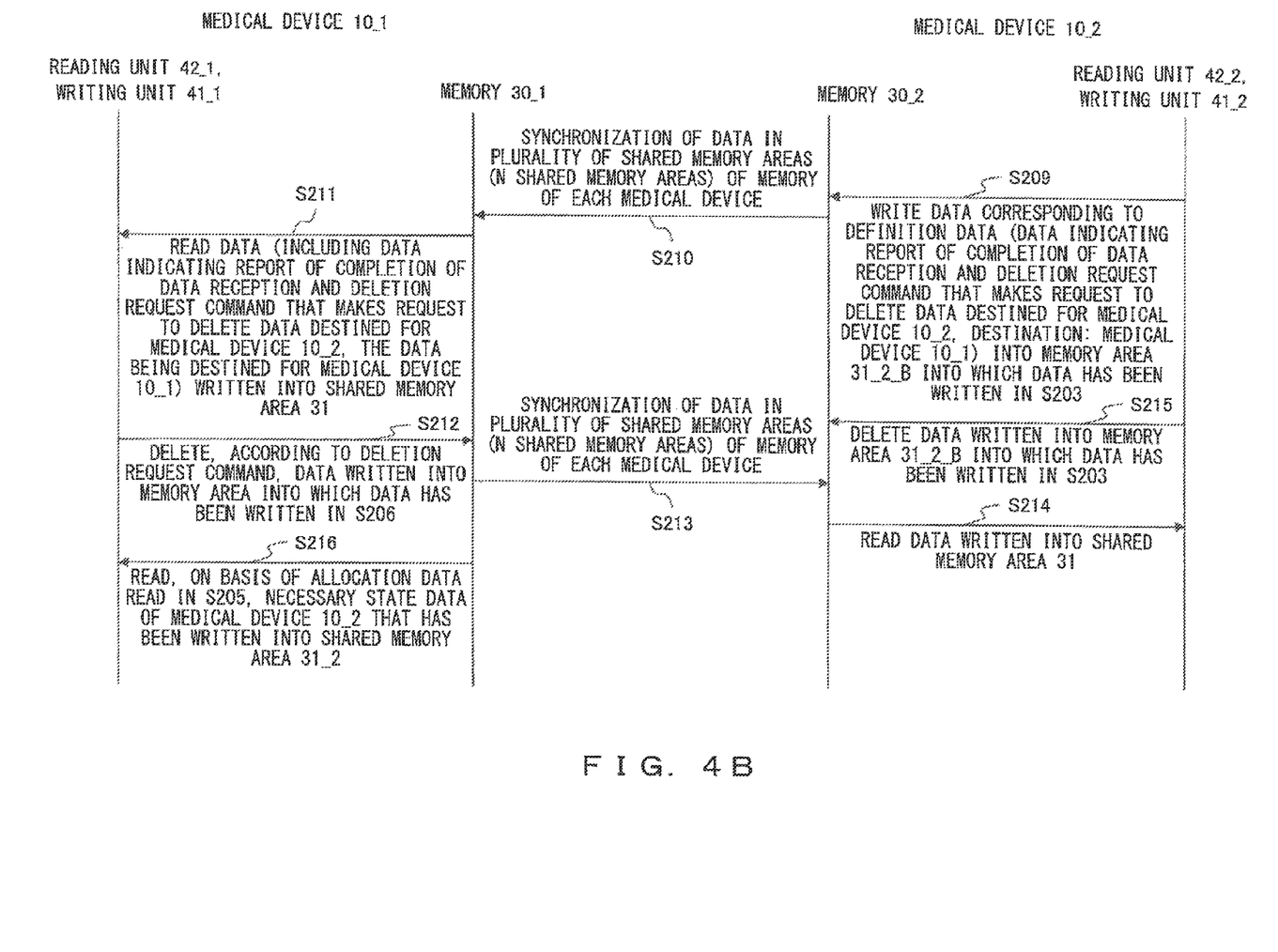
FIG. 4B is the sequence diagram (part 2) that illustrates an example of an operation performed when necessary device state data of a certain medical device is read by another medical device.

FIGS. 4A and 4B are a sequence diagram that illustrates an example of an operation performed when necessary device state data of the medical device 10_2 is read by the medical device 10_1.

As illustrated in FIGS. 4A and 4B, in this operation, first, the writing unit 41_2 of the medical device 10_2 writes, into a memory area (hereinafter referred to as a "memory area 31_2_A") included in the shared memory area 31_2 of the memory 30_2 and as definition data that defines a method for using the memory area 31_2_A, data that defines the memory area 31_2_A being used for sharing device state data of the medical device 10_2 and data of an area size of the memory area 31_2_A, and writes, into the memory area 31_2_A and as data corresponding to the definition data, the device state data of the medical device 10_2 on the basis of allocation data indicating data allocation of the device state data of the medical device 10_2 (S201)

After that, synchronization of data is performed in the plurality of shared memory areas 31 (N shared memory areas) of the memory 30 of each of the medical devices 10 (S202). In S202, for example, the communication unit 20_1 of the medical device 10_1 reads data written into the shared memory area 31_2 of the memory 30_2 of the medical device 10_2 and writes the data into the shared memory area 31_2 of the memory 30_1.

Next, the writing unit 41_2 of the medical device 10_2 writes, into another memory area (hereinafter referred to as a "memory area 31_2_B") included in the shared memory area 31_2 of the memory 30_2 and as definition data that defines a method for using the memory area 31_2_B, data that defines the memory area 31_2_B being used for data transmission and data of an area size of the memory area 31_2_B, and writes, into the memory area 31_2_B and as data corresponding to the definition data, the allocation data described above and destination data indicating that the allocation data is to be destined for the medical device 10_1 (S203).

After that, synchronization of data is performed in the plurality of shared memory areas 31 (N shared memory areas) of the memory 30 of each of the medical devices 10 (S204). In S204, for example, the communication unit 20_1 of the medical device 10_1 reads data written into the shared memory area 31_2 of the memory 30_2 of the medical device 10_2 and writes the data into the shared memory area 31_2 of the memory 30_1, as in the case of S202.

Next, the reading unit 42_1 of the medical device 10_1 reads data written into the shared memory area 31 of the memory 30_1 (S205). In S205, for example, the reading unit 42_1 reads the allocation data destined for the medical device 10_1 from the shared memory area 31_2 of the memory 30_1.

Next, the writing unit 41_1 of the medical device 10_1 writes, into a certain memory area included in the shared memory area 31_1 of the memory 30_1 and as definition data that defines a method for using the certain memory area, data that defines the certain memory area being used for data transmission and data of an area size of the certain memory area, and writes, into the certain memory area and as data corresponding to the definition data, response data for the allocation data read in S205 (allocation data of the device state data of the medical device 10_2) and destination data indicating that the response data is to be destined for the medical device 10_2 (S206).

After that, synchronization of data is performed in the plurality of shared memory areas 31 (N shared memory areas) of the memory 30 of each of the medical devices 10 (S207). In S207, for example, the communication unit 20_2 of the medical device 10_2 reads data written into the shared memory area 31_1 of the memory 30_1 of the medical device 10_1 and writes the data into the shared memory area 31_1 of the memory 30_2.

Next, the reading unit 42_2 of the medical device 10_2 reads data written into the shared memory area 31 of the memory 30_2 (S208). In S208, for example, the reading unit 42_2 reads, from the shared memory area 31_1 of the memory 30_2, the response data, destined for the medical device 10_2, for the allocation data.

Next, as data corresponding to the definition data, the writing unit 41_2 of the medical device 10_2 writes, into the memory area 31_2_B which is included in the shared memory area 31_2 of the memory 30_2 and into which data has been written in S203, data indicating a report of a completion of data reception and a deletion request command that makes a request to delete data destined for the medical device 10_2, and destination data indicating that the data indicating the report and the deletion request command is to be destined for the medical device 10_1 (S209).

After that, synchronization of data is performed in the plurality of shared memory areas 31 (N shared memory areas) of the memory 30 of each of the medical devices 10 (S210). In S210, for example, the communication unit 20_1 of the medical device 10_1 reads data written into the shared memory area 31_2 of the memory 30_2 of the medical device 10_2 and writes the data into the shared memory area 31_2 of the memory 30_1, as in the cases of S202 and S204.

Next, the reading unit 42_1 of the medical device 10_1 reads data written into the shared memory area 31 of the memory 30_1 (S211). In S211, for example, the reading unit 42_1 reads, from the shared memory area 31_2 of the memory 30_1, the data destined for the medical device 10_1 which indicates a report of a completion of data reception and a deletion request command that makes a request to delete data destined for the medical device 10_2.

Next, according to the deletion request command, the writing unit 41_1 of the medical device 10_1 deletes data written into the certain memory area which is included in the shared memory area 31_1 of the memory 30_1 and into which data has been written in S206 (S212).

After that, synchronization of data is performed in the plurality of shared memory areas 31 (N shared memory areas) of the memory 30 of each of the medical devices 10 (S213). In S213, for example, the communication unit 20_2 of the medical device 10_2 reads data written into the shared memory area 31_1 of the memory 30_1 of the medical device 10_1 and writes the data into the shared memory area 31_1 of the memory 30_2, as in the case of S207. Accordingly, data written into a certain memory area that is included in the shared memory area 31_1 of the memory 30_2 and that corresponds to the certain memory area from which data has been deleted in S212 is also deleted.

Next, the reading unit 42_2 of the medical device 10_2 reads data written into the shared memory area 31 of the memory 30_2 (S214).

During a period of time from the point at which the process of S210 is terminated to the point just before the process of S213 is started, in the medical device 10_2, the writing unit 41_2 deletes data written into the memory area 31_2_B which is included in the shared memory area 31_2 of the memory 30_2 and into which data has been written in S203 and S209 (S215). Accordingly, in S213 described above, the communication unit 20_1 of the medical device 10_1 reads data written into the shared memory area 31_2 of the memory 30_2 of the medical device 10_2 and writes the data into the shared memory area 31_2 of the memory 30_1, which results in also deleting data written into a certain memory area that is included in the shared memory area 31_2 of the memory 30_1 and that corresponds to the memory area 31_2_B from which data has been deleted in S215.

After that, on the basis of the allocation data read in S205, the reading unit 42_1 of the medical device 10_1 reads necessary data in device state data of the medical device 10_2, the device state data having been written into the shared memory area 31_2 of the memory 30_1 (S216).

For example, the operation illustrated in FIGS. 4A and 4B permits the medical device 10_1 to read necessary device state data of the medical device 10_2.

As described above, the medical device system 1 according to the present embodiment makes it possible to perform transmission/reception of variable data (such as command data, allocation data, or response data) between specific medical devices 10 (for example, between the medical device 10_1 and the medical device 10_2), using the memory 30 included in each of the medical devices 10. Further, in each of the medical devices 10, allocation data of device state data of another medical device 10 is read, and necessary device state data of the another medical device 10 is read on the basis of the allocation data. Thus, for example, even if data allocation of device state data has been changed, it is possible to read necessary data in the device state data after the change in data allocation by reading allocation data that corresponds to the data allocation after the change.

The following modification may be made to the medical device system 1 according to the present embodiment.

For example, with respect to a certain memory area included in the shared memory area 31 of the memory 30, when data that defines the certain memory area being used for data transmission and data of an area size of the certain memory area are written into the certain memory area as definition data that defines a method for using the certain memory area, and when transmission data (such as command data) and destination data of the transmission data are written into the certain memory area as data corresponding to the definition data, a plurality of different pieces of destination data may be written into the certain memory area as the destination data. In this case, a different piece of transmission data may be written as transmission data for each piece of destination data.

The embodiments described above are just examples to facilitate understanding of the present invention, and the invention is not limited to these embodiments. Various modifications and alterations may be made hereto without departing from the spirit of the invention specified in the claims.

What is claimed is:

1. A medical device system comprising:
a first medical device;
a first memory provided in the first medical device;
a second medical device; and
a second memory provided in the second medical device, wherein
the first memory includes a first shared memory area allocated to the first medical device and a second shared memory area allocated to the second medical device,
the second memory includes a third shared memory area allocated to the first medical device and a fourth shared memory area allocated to the second medical device,
the first medical device includes
a first writing unit that dynamically writes, into a certain memory area included in the first shared memory area, definition data that defines a method for using the certain memory area and data corresponding to the definition data, and
a first synchronization unit that periodically reads data written into the fourth shared memory area and writes the read data into the second shared memory data, such that data written into the second shared memory area is identical to the data written into the fourth shared memory area, and
the second medical device includes
a second writing unit that dynamically writes, into a certain memory area included in the fourth shared memory area, definition data that defines a method for using the certain memory area and data corresponding to the definition data
a second synchronization unit that periodically reads data written into the first shared memory area and writes the read data into the third shared memory data, such that data written into the third shared memory area is identical to the data written into the first shared memory area.

2. The medical device system according to claim 1, wherein
the first medical device further includes a first reading unit that reads the data written into the second shared memory area, and
the second medical device further includes a second reading unit that reads the data written into the third shared memory area.

3. The medical device system according to claim 2, wherein
the first writing unit writes, into a certain memory area included in the first shared memory area and as definition data that defines a method for using the certain memory area, data that defines the certain memory area being used for data transmission and data of an area size of the certain memory area, and writes, into the certain memory area and as data corresponding to the definition data, command data and destination data indicating that the command data is to be destined for the second medical device,
when the command data which is destined for the second medical device is read by the second reading unit, the second writing unit writes, into a certain memory area included in the fourth shared memory area and as definition data that defines a method for using the certain memory area, data that defines the certain memory area being used for data transmission and data of an area size of the certain memory area, and writes, into the certain memory area and as data corresponding to the definition data, response data for the command data and destination data indicating that the response data is to be destined for the first medical device, and
the first reading unit reads the response data, destined for the first medical device, for the command data.

4. The medical device system according to claim 2, wherein
the second writing unit writes, into a certain memory area included in the fourth shared memory area and as definition data that defines a method for using the certain memory area, data that defines the certain memory area being used for data transmission and data of an area size of the certain memory area, and writes, into the certain memory area and as data corresponding to the definition data, command data and destination data indicating that the command data is to be destined for the first medical device,
when the command data which is destined for the first medical device is read by the first reading unit, the first writing unit writes, into a certain memory area included in the first shared memory area and as definition data that defines a method for using the certain memory area, data that defines the certain memory area being used for data transmission and data of an area size of the certain memory area, and writes, into the certain memory area and as data corresponding to the definition data, response data for the command data and destination data indicating that the response data is to be destined for the second medical device, and
the second reading unit reads the response data, destined for the second medical device, for the command data.

5. The medical device system according to claim 2, wherein
the first writing unit writes, into a certain memory area included in the first shared memory area and as definition data that defines a method for using the certain memory area, data that defines the certain memory area being used for sharing device state data of the first medical device and data of an area size of the certain memory area, and writes, into the certain memory area and as data corresponding to the definition data, the device state data of the first medical device on the basis of allocation data indicating data allocation of the device state data of the first medical device, the first writing unit writes, into another memory area included in the first shared memory area and as definition data that defines a method for using the another memory area, data that defines the another memory area being used for data transmission and data of an area size of the another memory area, and writes, into the another memory area and as data corresponding to the definition data, the allocation data and destination data indicating that the allocation data is to be destined for the second medical data, and the second reading unit reads the allocation data which is destined for the second medical device, and reads the device state data of the first medical device on the basis of the allocation data.

6. The medical device system according to claim 2, wherein the second writing unit writes, into a certain memory area included in the fourth shared memory area and as definition data that defines a method for using the certain memory area, data that defines the certain memory area being used for sharing device state data of the second medical device and data of an area size of the certain memory area, and writes, into the certain memory area and as data corresponding to the definition data, the device state data of the second medical device on the basis of allocation data indicating data allocation of the device state data of the second medical device, the second writing unit writes, into another memory area included in the fourth shared memory area and as definition data that defines a method for using the another memory area, data that defines the another memory area being used for data transmission and data of an area size of the another memory area, and writes, into the another memory area and as data corresponding to the definition data, the allocation data and destination data indicating that the allocation data is to be destined for the first medical device, and the first reading unit reads the allocation data which is destined for the first medical device, and reads the device state data of the second medical device on the basis of the allocation data.

7. A method for sharing a memory in a medical device system that includes a first medical device, a first memory in the first medical device, a second medical device, and a second memory in the second medical device, where the first memory includes a first shared memory area allocated to the first medical device and a second shared memory area allocated to the second medical device, and the second memory includes a third shared memory area allocated to the first medical device and a fourth shared memory area allocated to the second medical device, the method comprising:

dynamically writing, by the first medical device and into a certain memory area included in the first shared memory area, definition data that defines a method for using the certain memory area and data corresponding to the definition data;

dynamically writing, by the second medical device and into a certain memory area included in the fourth shared memory area, definition data that defines a method for using the certain memory area and data corresponding to the definition data;

periodically reading, by the first medical device, data written into the fourth shared memory area and writing, by the first medical device, the read data into the second shared memory data, such that data written into the second shared memory area is identical to the data written into the fourth shared memory area;

periodically reading, by the second medical device, data written into the first shared memory area and writing, by the second medical device, the read data into the third shared memory data, such that data written into the third shared memory area is identical to the data written into the first shared memory area;

reading, by the first medical device, the data written into the second shared memory area; and reading, by the second medical device, the data written into the third shared memory area.

8. A medical device system comprising:

a first medical device;
a first memory provided in the first medical device;
a second medical device; and
a second memory provided in the second medical device, wherein the first memory includes a first shared memory area allocated to the first medical device and a second shared memory area allocated to the second medical device, the second memory includes a third shared memory area allocated to the first medical device and a fourth shared memory area allocated to the second medical device, the first medical device includes a first processor programmed to:

dynamically write, into a certain memory area included in the first shared memory area, definition data that defines a method for using the certain memory area and data corresponding to the definition data, and periodically read data written into the fourth shared memory area and write the read data into the second shared memory data, such that data written into the second shared memory area is identical to the data written into the fourth shared memory area, and the second medical device includes a second processor programmed to:

dynamically write, into a certain memory area included in the fourth shared memory area, definition data that defines a method for using the certain memory area and data corresponding to the definition data periodically read data written into the first shared memory area and write the read data into the third shared memory data, such that data written into the third shared memory area is identical to the data written into the first shared memory area.

9. The medical device system according to claim 8, wherein the first processor is further programmed to:
read the data written into the second shared memory area, and the first processor is further programmed to:
read the data written into the third shared memory area.

10. The medical device system according to claim 9, wherein the first processor writes, into a certain memory area included in the first shared memory area and as definition data that defines a method for using the certain memory area, data that defines the certain memory area being used for data transmission and data of an area size of the certain memory area, and writes, into the certain memory area and as data corresponding to the definition data, command data and destination data indicating that the command data is to be destined for the second medical device, when the command data which is destined for the second medical device is read by the second processor, the second processor writes, into a certain memory area included in the fourth shared memory area and as definition data that defines a method for using the certain memory area, data that defines the certain memory area being used for data transmission and data of an area size of the certain memory area, and writes, into the certain memory area and as data corresponding to the definition data, response data for the command data and destination data indicating that the response data is to be destined for the first medical device, and the first processor reads the response data, destined for the first medical device, for the command data.

11. The medical device system according to claim 9, wherein the second processor writes, into a certain memory area included in the fourth shared memory area and as definition data that defines a method for using the certain memory area, data that defines the certain memory area being used for data transmission and data of an area size of the certain memory area, and writes, into the certain memory area and as data corresponding to the definition data, command data and destination data indicating that the command data is to be destined for the first medical device, when the command data which is destined for the first medical device is read by the first processor, the first processor writes, into a certain memory area included in the first shared memory area and as definition data that defines a method for using the certain memory area, data that defines the certain memory area being used for data transmission and data of an area size of the certain memory area, and writes, into the certain memory area and as data corresponding to the definition data, response data for the command data and destination data indicating that the response data is to be destined for the second medical device, and the second processor reads the response data, destined for the second medical device, for the command data.

12. The medical device system according to claim 9, wherein the first processor writes, into a certain memory area included in the first shared memory area and as definition data that defines a method for using the certain memory area, data that defines the certain memory area being used for sharing device state data of the first medical device and data of an area size of the certain memory area, and writes, into the certain memory area and as data corresponding to the definition data, the device state data of the first medical device on the basis of allocation data indicating data allocation of the device state data of the first medical device, the first processor writes, into another memory area included in the first shared memory area and as definition data that defines a method for using the another memory area, data that defines the another memory area being used for data transmission and data of an area size of the another memory area, and writes, into the another memory area and as data corresponding to the definition data, the allocation data and destination data indicating that the allocation data is to be destined for the second medical data, and the second processor reads the allocation data which is destined for the second medical device, and reads the device state data of the first medical device on the basis of the allocation data.

13. The medical device system according to claim 9, wherein the second processor writes, into a certain memory area included in the fourth shared memory area and as definition data that defines a method for using the certain memory area, data that defines the certain memory area being used for sharing device state data of the second medical device and data of an area size of the certain memory area, and writes, into the certain memory area and as data corresponding to the definition data, the device state data of the second medical device on the basis of allocation data indicating data allocation of the device state data of the second medical device, the second processor writes, into another memory area included in the fourth shared memory area and as definition data that defines a method for using the another memory area, data that defines the another memory area being used for data transmission and data of an area size of the another memory area, and writes, into the another memory area and as data corresponding to the definition data, the allocation data and destination data indicating that the allocation data is to be destined for the first medical data, and the first processor reads the allocation data which is destined for the first medical device, and reads the device state data of the second medical device on the basis of the allocation data.

* * * * *